United States Patent
Van Rens et al.

(10) Patent No.: US 10,265,728 B2
(45) Date of Patent: Apr. 23, 2019

(54) MONOLITHICALLY INTEGRATED THREE ELECTRODE CMUT DEVICE

(71) Applicant: KONINKLIJKE PHILIPS N.V., Eindhoven (NL)

(72) Inventors: Antonia Cornelia Van Rens, Nuenen (NL); Alfons Wouter Groenland, Valkenswaard (NL)

(73) Assignee: Koninklijke Philips N.V., Eindhoven (NL)

( * ) Notice: Subject to any disclaimer, the term of this patent is extended or adjusted under 35 U.S.C. 154(b) by 486 days.

(21) Appl. No.: 15/103,388

(22) PCT Filed: Dec. 4, 2014

(86) PCT No.: PCT/EP2014/076475
§ 371 (c)(1),
(2) Date: Jun. 10, 2016

(87) PCT Pub. No.: WO2015/086413
PCT Pub. Date: Jun. 18, 2015

(65) Prior Publication Data
US 2016/0310992 A1   Oct. 27, 2016

(30) Foreign Application Priority Data
Dec. 12, 2013   (EP) .................................... 13196881

(51) Int. Cl.
*B06B 1/02* (2006.01)
*A61B 8/00* (2006.01)

(52) U.S. Cl.
CPC .......... *B06B 1/0292* (2013.01); *A61B 8/4444* (2013.01); *A61B 8/4494* (2013.01); *B06B 2201/20* (2013.01)

(58) Field of Classification Search
CPC . B06B 1/0292; B06B 2201/20; A61B 8/4494; A61B 8/4444
See application file for complete search history.

(56) References Cited

U.S. PATENT DOCUMENTS

| | | | |
|---|---|---|---|
| 5,396,143 A | 3/1995 | Seyed-Bolorforosh et al. | |
| 8,105,941 B2 | 1/2012 | Huang | |
| 2004/0174773 A1 | 9/2004 | Thomenius et al. | |
| 2008/0269614 A1 | 10/2008 | Adachi et al. | |
| 2009/0016606 A1 | 1/2009 | Meyer et al. | |

(Continued)

FOREIGN PATENT DOCUMENTS

| | | | | |
|---|---|---|---|---|
| CN | 105828962 A | * | 8/2016 | ........... B06B 1/0292 |
| CN | 106999984 A | * | 8/2017 | ........... B06B 1/0292 |

(Continued)

*Primary Examiner* — Daniel Pihulic

(57) ABSTRACT

A capacitive micromachined ultrasonic transducer (CMUT) cell comprising three electrodes: a first electrode coupled to a cell membrane; a second electrode embedded into a cell floor opposing the first electrode and separated therefrom by a gas or vacuum cavity; and a third electrode opposing the second electrode on the cavity side, wherein a dielectric layer is sandwiched between the second electrode and the third electrode to create a capacitive relation between the second electrode and the third electrode. The three electrode CMUT cell provides an ultrasound transducer with two actively driven (controlled) electrodes.

14 Claims, 7 Drawing Sheets

(56) References Cited

U.S. PATENT DOCUMENTS

2016/0310992 A1* 10/2016 Van Rens ............. B06B 1/0292
2017/0320091 A1* 11/2017 Budzelaar ............ B06B 1/0292

FOREIGN PATENT DOCUMENTS

| EP | 1944070 A1 | 7/2008 | |
|----|----|----|----|
| EP | 1897498 A1 | 12/2008 | |
| EP | 2168493 A1 | 3/2010 | |
| EP | 3079837 A1 * | 10/2016 | ........... B06B 1/0292 |
| EP | 3229978 A1 * | 10/2017 | ........... B06B 1/0292 |
| WO | 2006123301 A2 | 11/2006 | |
| WO | 2009016606 A2 | 2/2009 | |
| WO | WO-2015086413 A1 * | 6/2015 | ........... B06B 1/0292 |
| WO | WO-2016091624 A1 * | 6/2016 | ........... B06B 1/0292 |

* cited by examiner (a)

(b)

MONOLITHICALLY INTEGRATED THREE ELECTRODE CMUT DEVICE

This application is the U.S. National Phase application under 35 U.S.C. § 371 of International Application No. PCT/EP2014/076475, filed on Dec. 4, 2014, which claims the benefit of European Application Serial No. 13196881.0, filed Dec. 12, 2013. These applications are hereby incorporated by reference herein.

FIELD OF THE INVENTION

This invention relates to a capacitive micromachined ultrasonic transducer (CMUT) cell comprising a substrate, a cell membrane opposing the substrate with a gap there between, a first electrode coupled to the cell membrane, a second electrode embedded into a cell floor opposing the first electrode and separated therefrom by a gas or vacuum cavity, wherein the cell floor comprises an upper surface of the substrate. Further this invention relates to a probe comprising an array of the CMUT cells according to the present invention, and an ultrasonic imaging system comprising such the probe according to the present invention.

BACKGROUND OF THE INVENTION

Such a capacitive micromachined ultrasonic transducer cell, probe and imaging system are disclosed in EP1944070.

These products are used for medical diagnostic scans.

CMUT transducers are tens of micrometer size diaphragm-like cells that usually comprise two electrodes opposing each other. For transmission the capacitive charge applied to the electrodes is modulated to vibrate/move the diaphragm (membrane) of the device and thereby transmit a sound wave. Objects placed in the way of the sound wave propagation reflect the wave. The reflected sound wave causes vibrations of the membrane, modulating the capacitance between two electrodes of the CMUT transducer, thereby generating an electric signal. This signal is representative for the reflected sound wave hitting the membrane.

The CMUT cells are arranged in an array for high-frequency beam-forming.

For good performance, CMUTs require a high bias voltage (e.g. 100V) applied between the electrodes.

In the cases, where 3D imaging is not feasible (e.g. due to cost reasons, limited available area or required frame rate), a bi-plane 2D imaging may be applied.

In bi-plane imaging the array of CMUT's is divided in two groups of transducer elements arranged substantially along two directions, wherein each CMUT element can be activated within both groups. In the prior art this is realized by connecting all top electrodes of the elements in array to a metallized pattern having a main orientation along the x-direction and all bottom electrodes to a metallization pattern with main orientation along the y-direction. A DC source is supplied to each element of the group through an RC-filter (also known as bias-T filter). This bias T-filter separates the AC-component of the signal from the DC-component so that the ASIC technology for processing the detection signals of the probe only has to cope with the AC-component of the signal and is prevented from exposure to high voltage.

The bias-T filters in the array comprise a discrete high-voltage coupling capacitor and a discrete high impedance resistor for each interconnected element. In case of "N" elements in the group, "N" discrete high-voltage capacitors and the same amount of discrete resistors have to be provided. Due to the relatively large dimensions of these high-voltage components the application of the T-bias filters in CMUT arrays eliminates gained benefits of miniaturization and can be hardly implemented in ultrasound catheters, for example. Further, parasitic effects of these discrete components may limit the performance of the array.

SUMMARY OF THE INVENTION

It is an object of present invention to provide a capacitive micromachined ultrasonic transducer cell of the kind set forth in the opening paragraph which enables an improved and efficient high voltage supply to the CMUT array which is more suitable for miniaturization.

According to the invention this object is realized by providing a capacitive micromachined ultrasonic transducer cell comprising a third electrode, whereby the first or second electrode is capacitively coupled with the third electrode, whereby the capacitive coupling is realized by a dielectric layer sandwiched between and being in direct contact with the capacitively coupled electrodes.

This advantageous design of the CMUT cell, comprising three electrodes integrated into the cell, provides an improved CMUT device, wherein the ultrasound transducer and a capacitive component of the RC-filter are implemented within one CMUT cell. The separate third electrode is located in between of the two electrodes and has a capacitive relation with either of two electrodes of the CMUT cell, wherein the two electrodes are separated by the cavity. This capacitive coupling is realized by the dielectric layer sandwiched in between the capacitively coupled electrodes. Therefore, the third electrode is capacitively coupled to one of the two electrodes via the CMUT cavity and to another electrode through the dielectric layer, wherein the latter relation defines a capacitor for the integrated into the CMUT cell RC filter. Therefore, the stored charge related to the high bias voltage can be isolated from the user/patient by two conductive metal plates. In an embodiment of the present invention the third electrode is located in the cell floor opposing the second electrode from the cavity side.

This embodiment describes a particular realization of the three electrodes CMUT cell, wherein the third electrode is located in the cell floor, such as it opposes the second electrode from the cavity side. In this case for both, the second and the third electrodes, the separation distances to the first electrode comprise the CMUT cavity. The possible advantage for this configuration may be simplification of the CMUT manufacturing process, wherein two out of three electrodes are located in the non-vibrating floor of the CMUT cavity.

In an embodiment of the present invention the capacitive relation between the second electrode and the third electrode is larger than or equals to the capacitive relation between the third electrode and the first electrode.

In order to provide an efficient implementation of the RC filter capacitive component and avoid the signal attenuation the capacitor formed by the second and third electrodes shall be equal or larger than the capacitor defined by the CMUT cavity.

Yet in another embodiment of the present invention the dielectric layer comprises a layer of material with a high dielectric constant.

This condition is a consequence of the requirements to the capacitive relation between the second and the third electrodes. In order to keep this capacitance above the CMUT's capacitance the dielectric layer may be material with a high dielectric constant (so called high-k dielectrics). This will also allow avoiding leakage currents between the electrodes and achieving stability in the CMUT's operation. Since leakage currents are not desirable, nor is breakdown, a limitation may be put on reducing dielectric thickness (it is desired to withstand the applied bias voltage) and therefore it will limit the ratio of the capacitances (Cc/Cf).

In another embodiment of the present invention the capacitive micromachined ultrasonic transducer cell further comprises a DC source for causing a DC bias voltage to the third electrode in relation to the ground potential, and a signal transmitter/receiver (105) coupled to the first electrode and the second electrodes for causing/sensing vibration of the membrane.

The DC bias voltage is provided via the separate third electrode, while the signal transmitter/receiver (provided through the ASIC electronics) can drive and/or sense via coupling to the separate signal (first and second) electrodes. This electrode's configuration allows separating a DC bias component from the signal component. As a result the high voltage requirements of the ASIC technology can be reduced in case both the first and second electrodes are actively controlled. This also allows exploiting the advantages of driving the CMUT cell from both sides.

In yet another embodiment of the present invention the DC bias source is connected to the third electrode through a resistor (R) with impedance larger than the impedance between the first electrode and the third electrode at the resonance frequency of the CMUT cell.

This embodiment enables a fully integrated RC filter into the CMUT cell. The capacitive component is implemented through the dielectric layer in between the second electrode and the third electrode, while the high impedance component is implemented through the resistor connected in series with the third electrode and via which the DC voltage can be applied. Therefore, in this embodiment every transducer CMUT cell may have its own high impedance shielding resistor inside the bias-node connection. This results in a "failing cMUT cell" not causing large shortcut currents and therefore not causing breakdown of the whole array of the connected ASIC.

In a further embodiment of the present invention the probe comprises an array of the CMUT cells, which array comprises a first and second subgroup of the CMUT cells, wherein the first sub-group of CMUT cells having the first electrode interconnected along one of the two directions and the second sub-group of the CMUT cells having the second electrode interconnected along the another direction.

This embodiment explores an opportunity of driving each CMUT cell in the probe via both the first and second electrodes in an array. Interconnecting of the first electrodes in the first sub-group and the second electrodes in the second sub-group provides a possibility of using the same CMUT cell for both sub-groups and ability to drive each sub-group individually.

In yet another embodiment of the present invention the third electrodes of the CMUT cells in array are connected to the same DC bias voltage source via series resistors Applying the same DC bias voltage source simplifies the electronic interconnects in the probe and permits further scaling down of the ultrasound probe's dimensions.

These and other aspects of the invention will be apparent from and elucidated with reference to the embodiments described hereinafter.

DETAILED DESCRIPTION OF EMBODIMENTS

Figure 1:
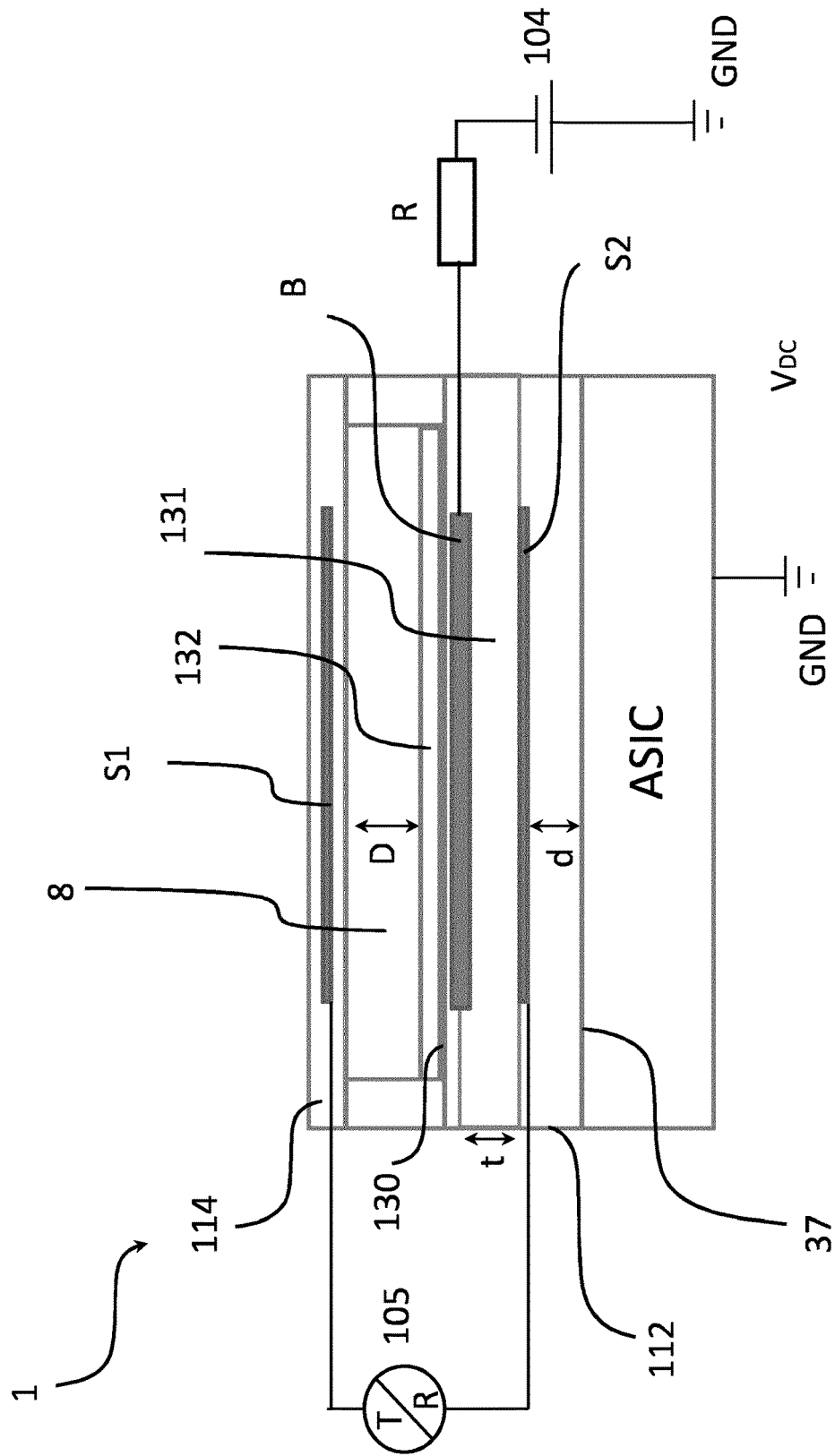
FIG. 1 illustrates a CMUT cell comprising three electrodes according to the principles of the present invention.

In an implementation of the present invention the elements of an ultrasound transducer array 10' (FIG. 8) comprise CMUT cells. FIG. 1 shows an embodiment of a CMUT cell 1 according to the invention. A flexible membrane or diaphragm 114 is suspended above (or oppossing) a substrate 112 with a gap 8 there between. The substrate can be made of either silicon or another CMOS compatible material such as glass. A first electrode S1 is coupled to the cell membrane 114 and can move with the membrane 114. In the embodiment shown in FIG. 1 a third electrode B is embedded into the floor 130 of the cell comprising an upper surface of the substrate 112. Other realizations of the electrode S1 design can be considered, such as electrode S1 may be embedded in the membrane 114 or it may be deposited on the membrane 114 as an additional layer. In this example, the bottom electrode B is circularly configured and embedded into the cell floor 130. In addition, the membrane layer 114 is fixed relative to the top face of the substrate layer 112 and configured and dimensioned so as to define a spherical or cylindrical cavity 8 between the membrane layer 114 and the substrate layer 112.

The cell and its cavity 8 may have alternative geometries. For example, cavity 8 could define a rectangular or square cross-section, a hexagonal cross-section, an elliptical cross-section, or an irregular cross-section. Herein, reference to the diameter of the CMUT cell shall be understood as the biggest lateral dimension of the cell.

Figure 2:
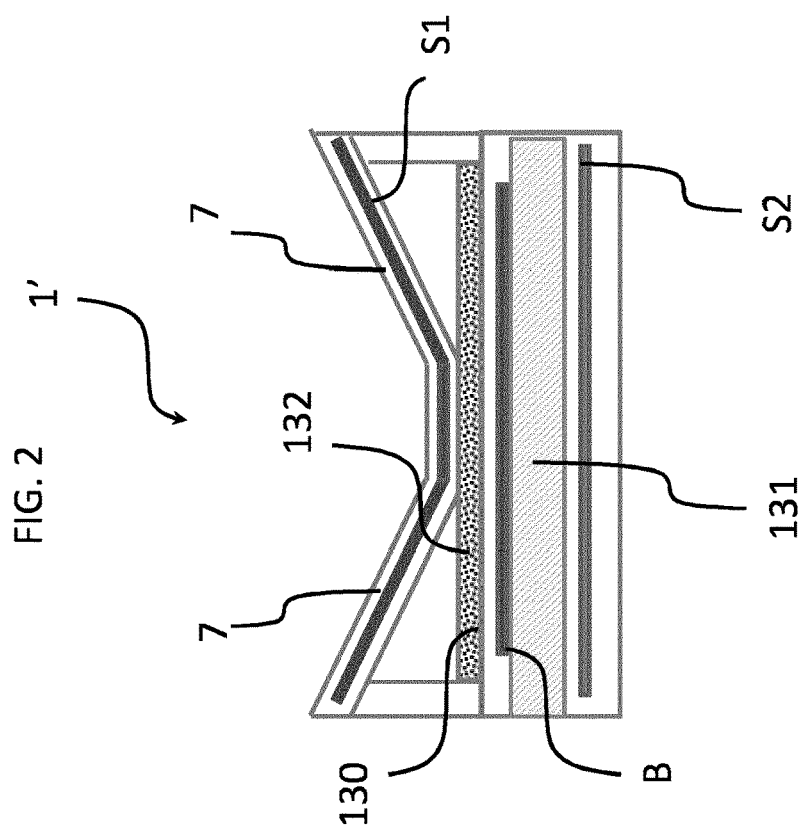
FIG. 2 illustrates a CMUT cell with collapsed membrane to the cell floor, FIG. 3 (a) depicts functional diagram of the CMUT cell with an integrated RC-filter; (b) depicts a symbolic representation of the CMUT cell of the present invention; (c) illustrates schematic representation of the main elements of the CMUT cell in accordance to the principles of the present invention, FIG. 4 (a) illustrates on-chip implementation of the high impedance resistor into the CMUT cell; (b) illustrated an integration of the resister into the substrate of the CMUT cell; (c) illustrated a combined integration of the third electrode and the high impedance resistor, FIG. 5 (a) illustrates an implementation of the signal transmitter/receiver using a differential circuit configuration during transmission of the signal; (b) illustrates an implementation of the signal transmitter/receiver using a differential circuit configuration during reception of the echo signal; (c) illustrates an implementation of the signal transmitter/receiver using a single ended circuit configuration with separate transmit and receive nodes.

The third electrode B is typically insulated on its cavity-facing surface with an additional insulating layer 132. A preferred insulating layer is a silicon dioxide (SiO2) dielectric layer deposited in a tetra ethyl oxysilane (TEOS) based PECVD process, formed above the third electrode B and below the first electrode S1. An alternative material for the insulating layer 132 can be oxide-nitride-oxide (ONO), high-k dielectrics and oxides (aluminium oxide, various grades including silane, SiH4, based PECVD SiO2). High-k dielectrics and oxides can be also deposited using atomic layer deposition (ALD) technique. The insulating layer may advantageously reduce charge accumulation which leads to device instability and drift and reduction in acoustic output pressure. Use of the insulating layer is desirable with CMUTs with collapsed membrane, which will be described hereinafter with reference to FIG. 2. This type of CMUT is more susceptible to charge retention than CMUTs operated with suspended membranes. The disclosed components may be fabricated from CMOS compatible materials, e.g., Al, Ti, nitrides (e.g., silicon nitride), oxides (various grades: thermal or TEOS/SiH4 LPCVD/PECVD based), oly-silicon and the like. In a CMOS fabrication, for example, the oxide and nitride layers may be formed by chemical vapor deposition and the metallization (electrode) layer put down by a sputtering process. Suitable CMOS processes are LPCVD and PECVD, the latter having a relatively low operating temperature of less than 400° C. Exemplary techniques for producing the disclosed cavity 8 involve defining the cavity in an initial portion of the membrane layer 114 before adding a top face of the membrane layer 114. In the exemplary embodiment depicted in FIG. 1, the diameter of the cavity 8 may be larger than the diameter of the second electrode B. First electrode S1 may have the same outer diameter as the third electrode B, although such conformance is not required. Thus, in an exemplary implementation of the present invention, the first electrode S1 is fixed relative to the top face of the membrane layer 114 so as to align with the third electrode B below.

The CMUT fabrication process can comprise either the "sacrificial release process", wherein the cavity underneath of the membrane is formed by first applying a sacrificial layer on the substrate, then applying the membrane layer followed by the removing of the sacrificial layer with a selective etchant; or the "wafer bonding process", wherein the cavity is formed on the prime wafer and the membrane in another wafer, then both wafers are bonded together such as the cavity confined by the membrane is formed (B. T. Khuri-Yakub, J. Micromech. Microeng. 21 (2011) 054004).

In accordance with principles of the present invention a second electrode S2 of the CMUT cell is deposited onto the substrate 112 opposing the third electrode B on the side opposite to the cavity 8. Thus, the third electrode B is located in between the first electrode S1 and the second electrode S2. A dielectric layer 131 with a thickness "t" is in direct contact and sandwiched between the second and the third electrodes; thus, providing a capacitive relation between these two electrodes.

The first S1 and third B electrodes of the CMUT cell provide the capacitive plates of the CMUT device and a gap of the cavity 8 having a thickness "D" in combination with the additional insulating layer 132 form the dielectric between the plates of the capacitor.

The first electrode (S1) can be brought in vibration by means of a signal transmitter/receiver 105 adapted to apply an AC voltage over the second S2 and first S1 electrodes, which result in the generation of an acoustic beam. When lateron the membrane vibrates as a result of the received acoustic signal, the changing dimension of the dielectric gap between the electrodes leads to changing capacitance of the CMUT which is detected by the signal transmitter/receiver 105, coupled to the membrane and second electrodes, as the response of the CMUT cell to a received acoustic echo.

CMUT device sensitivity can improved by increasing electric field through the cavity 8, which may be achieved following ways: 1) reduced effective dielectric thickness of the cMUT, defined by the spacing and dielectric constant of the dielectric between the first and third electrodes and 2) increased amount of "free" charge collected on the electrodes. The effective dielectric thickness is reduced in the collapsed mode, which is achieved by applying sufficient DC voltage; and the amount of the collected charge can be increased with increasing the DC bias voltage.

The spacing between the CMUT electrodes (S1 and B) is controlled by applying a DC bias voltage to the third electrode B from a DC bias source 104. For transmission the first electrode S1 and the second electrode S2 are driven (controlled) by an r.f. generator (generalized as the signal transmitter/receiver 105) whose a.c. signal causes the membrane to vibrate and transmit an acoustic signal. The substrate 112 of the CMUT cell 1 can be coupled to a top surface 37 of the application specific circuitry (ASIC) layer, wherein the distance between the second electrode S2 and the top surface 37 of the ASIC layer is denoted as "d". Commonly the distance "d" can be defined by so called "buried oxide" layer (not shown in the figure), that has an insulating function for the second electrode S2 towards the integrated circuit electronics (ASIC in this example). The "buried oxide" layer can be a silicon oxide layer with the thickness of around 2 micrometer. Though in FIG. 1 the signal transmitter/receiver 105 is depicted as a separated element, it shall be understood that the signal transmitter/receiver 105 may be implemented as a part of the circuitry electronics provided by ASIC. The CMUT cell can be either manufactured on top of the ASIC in a sequence of CMOS processes or attached to the ASIC through a flip-chip technique, for example.

Figure 3:
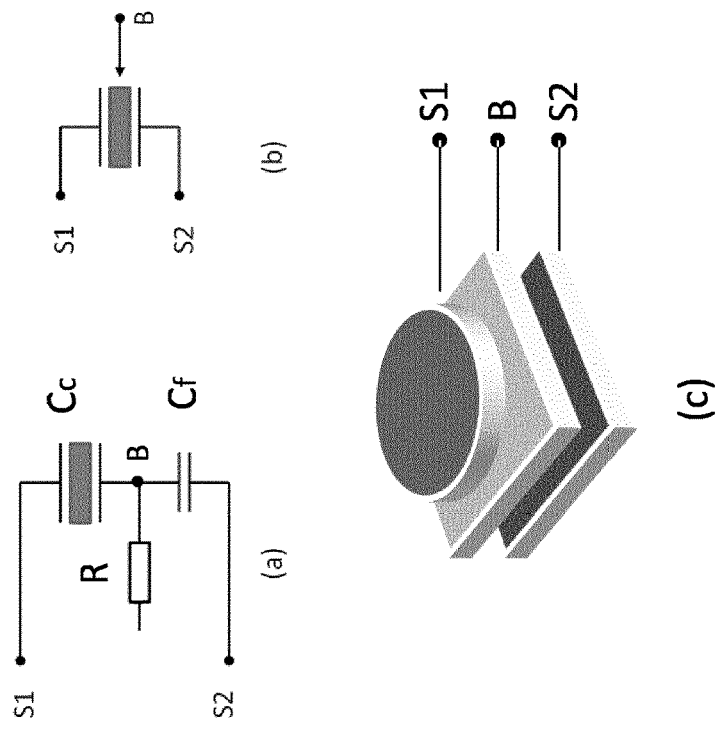

FIG. 3 illustrates a preferred and non-limiting example of the CMUT cell operation, wherein the membrane 114 of the CMUT cell 1' is a collapsed membrane. The collapsed membrane 7 during the CMUT operation may be made collapsed relative to the cell floor 130 and the suspended portions 7 of the membrane can be adapted to move/vibrate under applied electrical signal in between electrodes. From technology point of view, the CMUT with collapsed membrane can in principle be manufactured in any conventional way, comprising steps of providing a CMUT with a membrane and applying different means, such as electrical (bias voltage), mechanical, membrane stress or pressure, in order to bring the membrane to a collapsed state.

In the collapsed mode the CMUT capacitance is determined mainly by the additional insulating layer 132 and applied voltage. For example, a circular CMUT device having diameter of 60 micrometer may have 500 nm thick additional insulating layer. The CMUT capacitance is around 0.04 pF at zero applied DC voltage and around 0.1 pF (2.5 times higher) in the collapsed mode at 140V DC bias voltage. For other CMUT geometries, this ratio may vary.

The implementation of second electrode S2 in the substrate of the CMUT cell permits to separate an a.c. signal component from the DC bias voltage commonly applied to the CMUT device. This reduces the dimensions of the CMUT related electronics in ultrasound probe, in case both signal (membrane and substrate) electrodes are actively controlled.

One of the ways to arrange the CMUT devices in an array, in particular for bi-plane imaging, is providing a network of RC filters to the CMUT array, wherein a DC bias voltage is applied to each CMUT device through the RC filter. In this arrangement the CMUT array will comprise a discrete high-voltage coupling capacitor and a discrete high impedance resistor for each interconnected CMUT device. The dimensions of the discrete RC filter components may be disadvantageous for scaling down an ultrasound probe comprising the CMUT array.

The three electrode CMUT cell according to the principles of the present invention represents a CMUT device with an integrated capacitive part of the RC filter as described in detail hereinafter with reference to FIG. 3. The third electrode B is used to provide a DC bias voltage to the CMUT cell, while the capacitive part of the integrated RC filter is realized through the conductive plates of the third electrode B and the second electrode S2 separated by the dielectric layer 131.

Referring to FIG. 3A, in preferred embodiment in order to provide an efficient RC-filtering the capacitive relation Cf between the third B and the second S2 electrodes shall be equal or larger than the CMUT capacitive relation Cc (i.e. CMUT device capacitance) in between the membrane S1 and the third B electrodes. This condition results from the fact that for high frequencies, the series connection of Cc and Cf causes an attenuation of the signal according to (Cc+Cf)/Cf, the higher Cf is the lower signal is attenuated. The signal attenuation happens during both transmission and reception and may be limited by increasing Cf. In case of fixed Cc, the condition of CfCc can be realized by tuning the thickness "t" of the dielectric layer 131 and/or a dielectric constant of the material of the layer. The value of the capacitance Cf of the integrated RC-filter can be further improved by increasing overlap areas of the third B and the second S2 electrodes in relation to the first electrodes. An example of this is illustrated in FIG. 3C (for simplification reasons only main elements of the CMUT cell relevant for current embodiment are shown), wherein the circular shape first electrode S1 has smaller diameter than the dimensions of the third B and the second S2 electrodes, both having equal square shape. Note typical Cc value scales with the number of the CMUT cells in the array.

The dielectric layer 131 can be made of commonly known insulating materials, such as silicon dioxide, nitrides (e.g., silicon nitride) or high-k dielectrics. The dielectric layer 131 can also comprise multi-layers (e.g. ONO). In a CMOS fabrication, for example, the oxide and nitride layers may be formed by chemical vapor deposition. Suitable CMOS processes are also LPCVD and PECVD, the latter having a relatively low operating temperature of less than 400° C.

For example, a typical capacitance of an elliptical cross section CMUT cell having diameter of 60 micrometer is Cc=0.04 pF or 0.1 pF at a DC bias voltage of 0V (non-collapsed mode) or 140V (collapsed mode) respectively. Therefore, for optimal three electrode CMUT's operation the capacitance of the RC-filter shall be at least equal to the afore mentioned Cc values. From the preferred capacitance value and knowing the dielectric constant of the dielectric layer 131, one can calculate the preferred thickness "t" of the layer 131. In this example, using silicon dioxide ($\varepsilon$=3.9), t<2630 nm in non-collapse operation of the CMUT cell or t=<1050 nm in the collapsed mode of the CMUT cell operation. In practice, a ratio of 5 is preferred between Cc and Cf, wherein Cf>5*Cc. For the same geometry and layers stack this implies preferred silicon dioxide thicknesses of t<525 nm in non-collapsed or t<210 nm in collapsed modes of operation. Note that the layer thickness on the lower side is limited by the breakdown/bias voltage.

Another essential factor that can be taken into account while optimizing the Cf value is parasitic capacitance Cp towards the substrate 112 (mainly defined by the thickness "d"). This Cp may cause additional load on the circuitry electronics, while driving to or receiving from the second electrode S2. In order to avoid an a.c. signal leakage to the substrate 112 the Cp value is preferred to be lower than or equal to the CMUT's capacitance Cc: Cp<Cc. Thus, an improved performance of the CMUT cell comprising an integrated capacitive part of the RC-filter may be achieved by combining conditions of the optimal RC-filter performance (Cf≥Cc) and limitation of the parasitic capacitance influence (Cp<Cc). For the mentioned example of the elliptical CMUT cell a suitable thickness of the silicon oxide layer is above 5.25 micrometer or 2.1 micrometer for the collapsed mode. In practice, a factor 2 or 5 is between Cp and Cc is preferred, wherein Cp<Cc/2 or Cp<Cc/5. In the latter case, this implies a preferred oxide thickness of a factor 2.5 higher (i.e. above 13.1 micrometer or above 5.2 micrometer in the collapsed mode).

However other thicknesses "t" and "d" are also possible. Their exact values depend on the cut-off frequency required for the RC filter implementation for each given CMUT cell (array).

The present invention may be not limited to the particular embodiment. It shall be understood by the person skilled in the art that the third electrode may be also implemented into the membrane layer 114, wherein the dielectric layer 131 may be located in the membrane layer 114 and capacitively isolating the first electrode S1 and the third electrode. The capacitive part of the RC filter (Cf) will be defined by the capacitive relation of the third electrode and the first electrode.

In a further embodiment of the present invention, the DC bias source (104) is connected to the third electrode through a high impedance resistor (R) as schematically shown in FIG. 3A. For the convenience a symbolic representation of the three electrode CMUT cell is shown in FIG. 3B. This embodiment describes a full integration of all RC-filter components into the CMUT cell. The resistor can be implemented as a conductive layer, for example shaped in meander. The resistance of the meander equals to the product of the resistivity of the used conductive material with the conductive path length divided by the cross section area of the conductive layer. In case of the meander the resistance of the resistor may be tuned by changing the lengths of the meander, its thickness and conductive material choice.

In order to prevent the signal leakage through the third electrode B the preferred value of the resistance of the high impedance resistor R is about an order of magnitude higher than the impedance of the CMUT cell at the given operation frequency.

For example, for the 2D array operating at frequency f=5 MHz the CMUT capacitance value is around Cc=0.5 pF (for the diameter of 120 micrometer and collapsed mode of operation). The CMUT cell impedance Z=1/(2πfCc)=63 kOhm. Thus the preferred value of the resistance R may be higher than or equal ton 500 kOhm.

Another example, for the 1D array comprising 42 CMUT cells with the same diameter and operating at the same frequency as in the previous example, the Cc value will scale with cell number C_c=0.5*42=21 pF. Thus compared to the previous example the preferred value high impedance resistor will be reduced by the number of the elements in the 1D array R>500/42=11.9 kOhm. Note, the cuttof frequency of the integrated RC filter is also determined by the resistor value.

Figure 4:
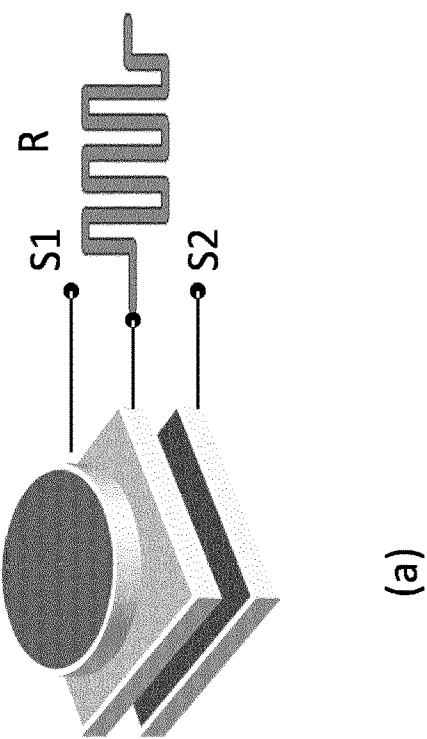
Figure 4:
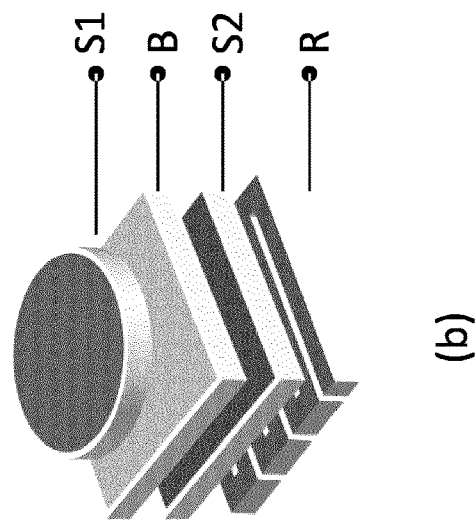

As illustrated in FIG. 4A the resistor may be an on-chip resistor (integrated into the substrate 112), e.g. located next to the CMUT cell. In FIG. 4B another embodiment is shown, wherein the resister R is integrated deeper (in the direction facing the top surface 37 of the ASIC) into the substrate under the second electrode S2. This embodiment permits even further minimizing of the CMUT array, wherein interconnect between the third electrode S2 and high impedance resistor R may be implemented through an interlayer metal contact (i.e. via).

The preferred conductive materials for the resistor's implementation are materials that are CMOS compatible and having a relative high resistivity, such as TiW, NiCr or poly silicon having resistivities of 70/100-150/>250 microOhm·cm.

Figure 5:
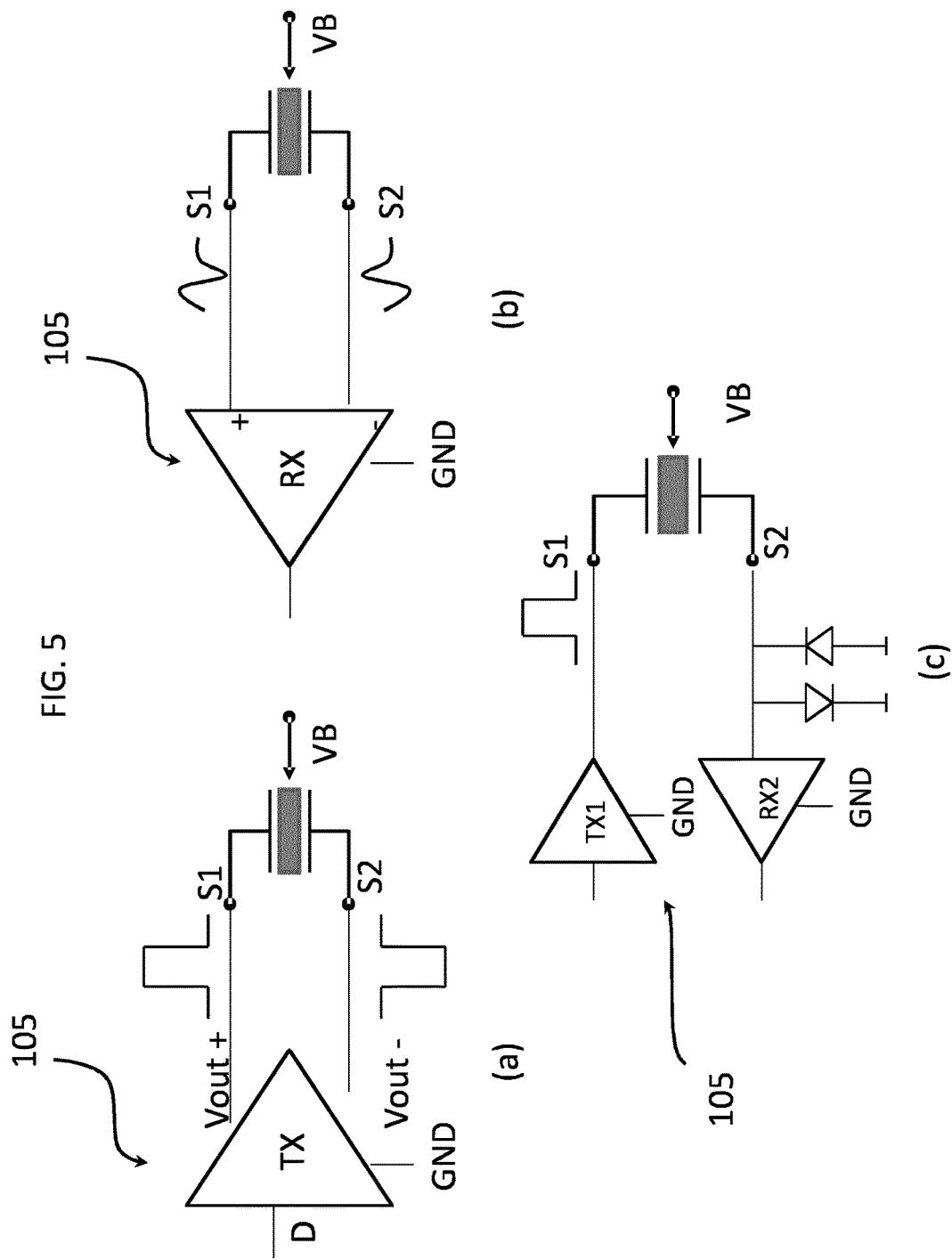

Referring to FIG. 5A, another embodiment of the present invention describes the specific implementation of the signal transmitter/receiver 105 during the transmission of the ultrasound signal by means of fully differential electronics. The possibility of the decoupling of the DC bias voltage, simplifies the implementation of differential electronics in the transducer. The important advantage of the differential electronics applied to the three electrodes CMUT is a reduction of the supply voltage required to activate the signal transmission. The first electrode S1 and the second electrode S2 may be coupled to a differential output Tx of a high voltage transmit pulser, wherein the effective amplitude of the driving signal is the difference between the a.c. signal applied to the first electrode S1 (Vout+) and the second electrode S2 (Vout−) and can be up to twice the amplitude of the supply voltage (2×Vout). This electronics configuration at the transmission mode results in minimized distortion of the second signal harmonics and well defined current loops, wherein signal is not passing through bias node.

In practice this means that the a.c. supply voltage can be lower (e.g. 30V instead of 60V) which reduces the voltage requirements of the ASIC technology as well as the requirements on voltage regulations of the transducer system such as creepage. Note that the required bias voltage still is high but this third electrode B does not need to provide any relevant current. Therefore, a high impedance series resistor e.g. 1 MOhm may be integrated in the system for safety reason.

For using a similar differential electronics realization of the signal transmitter/receiver 105 during the reception of the echo signal the first S1 and the second S2 electrodes may be coupled to a differential input Rx of a low noise receive amplifier as illustrated in FIG. 5B. As in the transmission case this minimizes distortion of the second signal harmonics and brings well defined current loops, better power supply rejection ration (PSRR) and reduced cross-talk between the CMUT cells. Yet another possibility of implementing transmission and reception of the signal in accordance with the principles of the present invention is illustrated in FIG. 5C. During transmission one of the signal electrodes (in the example, the first electrode S1) may be coupled to the output Tx1 (high voltage transmit pulser). During reception the other signal electrode (in the example, the second electrode S2) may be coupled to the input Rx2 (low noise receive amplifier). Due to the decoupling of the DC bias-voltage, the "grounds" (GND) of the TX and RX can be identical which simplifies the electronics and improves power supply rejection ratio. Furthermore, it is feasible to realize the receiver electronics using low-voltage components only, which improves receiver performance. Next to that, parasitic capacitance caused by the transmitter will hardly influence the performance of the receiver. Finally, the commonly used transmit-receive switch 16 (FIG. 8) is not needed in this embodiment due to separation of receive and transmit functions between two signal electrodes (S1 and S2).

Figure 6:
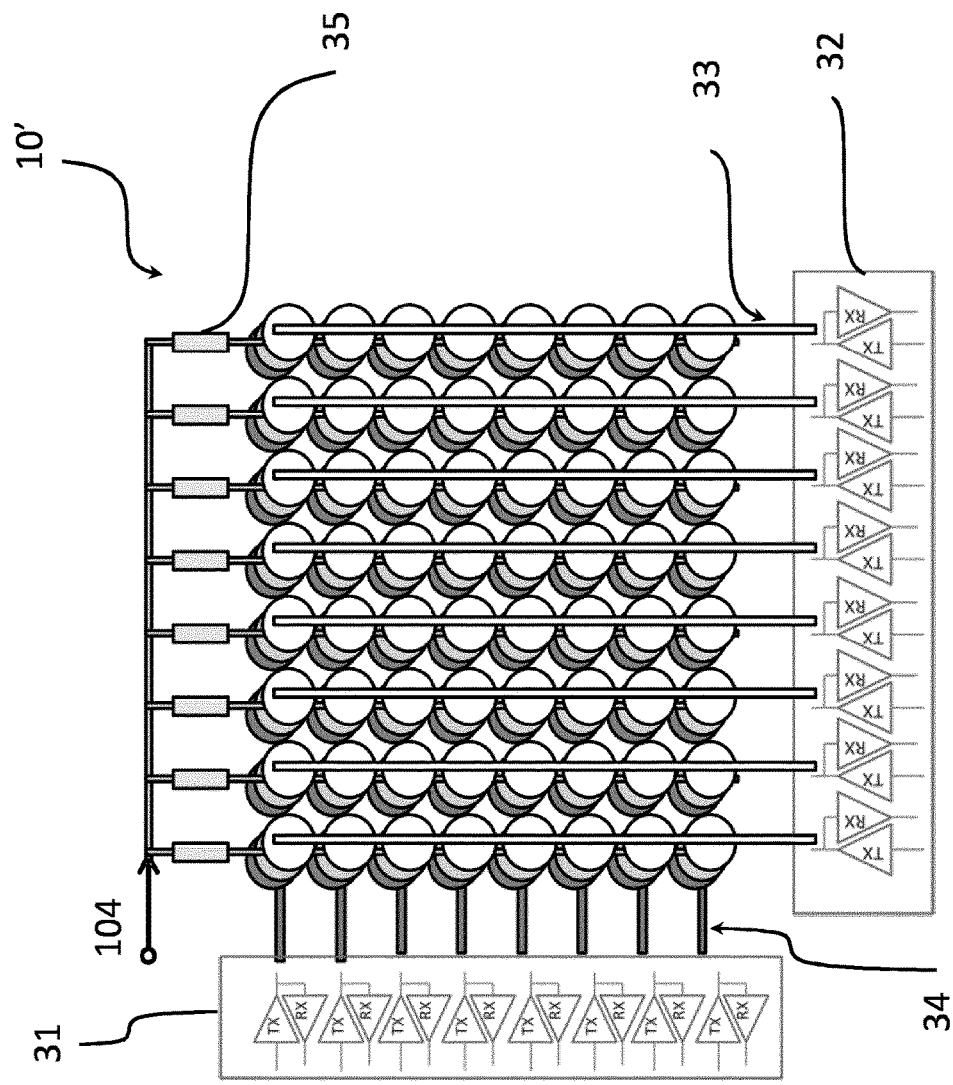
FIG. 6 depicts a 2D array of the CMUT cells arranged in the bi-plane configuration.

In a further embodiment of the present invention a two-dimensional (2D) array 10' of three electrode CMUTs is presented in FIG. 6. The CMUT cells in the array are arranged in a bi-plane imaging configuration. The array 10' comprises two sub-groups 33,34 of CMUT cells arranged substantially along two directions (horizontal and vertical in the non-limiting example of FIG. 6). A first sub-group 34 of the CMUT cells has the first electrode S1 interconnected along one of the two directions (horizontal in the given example) and a second sub-group 35 of the CMUT cells has the second electrode S2 interconnected along another direction (vertical in the given example). In this embodiment all CMUT cells of the array may be actively used in both "sub-groups" 33,34 by controlling the signal either through the first S1 or the second S2 electrodes.

Within the first sub-group 34 all cells along horizontal direction (rows) are interconnected and within the second sub-group 33 all cells along vertical direction (columns) are interconnected. This interconnects configuration allows an implementation of the bi-plane imaging in the ultrasound probe. Each row (column) multiple CMUT cells can be activated in parallel and can represent one transducer element. Therefore, the elements of each sub-group of the CMUTs may represent a one-dimensional ultrasound array. The two-dimensional array 10' comprising such sub-groups will have N×M elements, wherein N is number of elements (rows) in the first sub-group and M is the number of elements (columns) in the second sub-group. The rows and columns are connected to the signal transmitter/receivers circuitry of the first sub-group 31 and the second sub-group 32. By activating the row circuitry 31, while grounding the column circuitry 32, beamsteering is feasible "out of plane" in the vertical direction; and activation of the column circuitry 32, while grounding the row circuitry 31, beamsteering is feasible "out of plane" in the horizontal direction. In the array 10' the third electrodes of the cells may be either connected to the separate DC bias sources (not shown) or have a common connection to one DC bias source 104. In the latter case only one high impedance resistor 35 may be implemented for each element of either one of the sub-groups. The orientation of the direction of the bias-electrode connection equals to the direction of the second S2 electrode interconnection.

This embodiment of bi-plane 2D imaging has a particular potential in cases, where 3D imaging is not feasible (e.g. due to cost reasons, limited available area or required frame rate) and in cases where normal 2D imaging is not sufficient e.g. for in-body ultrasound imaging.

Figure 7:
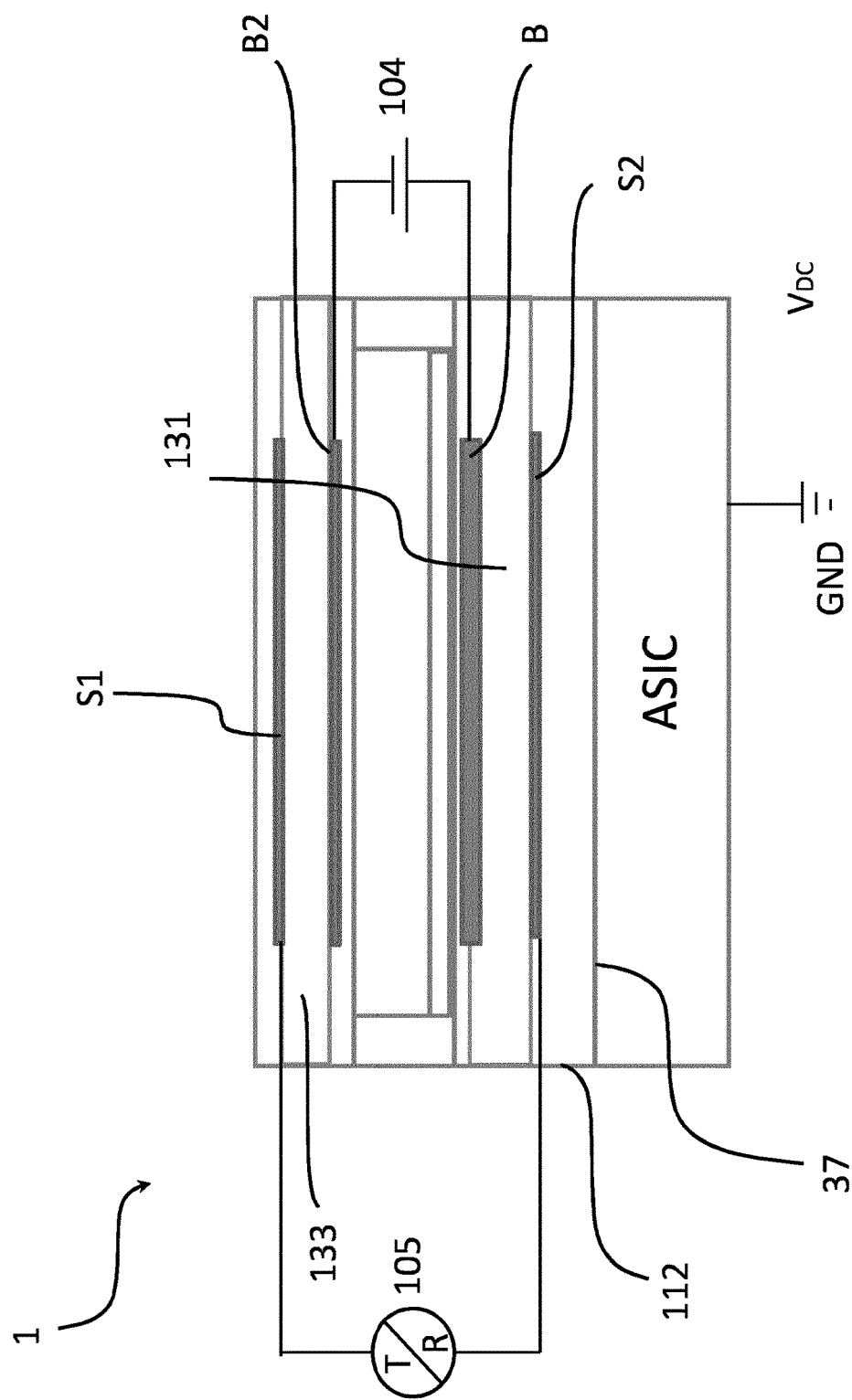
FIG. 7 illustrates the CMUT cell comprising three electrodes and an additional bias electrode B2 according to embodiment of the present invention.

In yet another embodiment of the present invention the CMUT cell may comprise an additional bias electrode B2 located such that the third electrode B and the additional bias electrode B2 are opposing each other through the cavity of the CMUT cell as illustrated in FIG. 7. For the convenience some of the repeating reference signs are not shown. In this embodiment the DC bias voltage is applied in between the third B and the additional bias electrode B2. The additional bias electrode may be embedded into the membrane and may be electrically separated from the first electrode S1 with a membrane dielectric layer 133.

Figure 8:
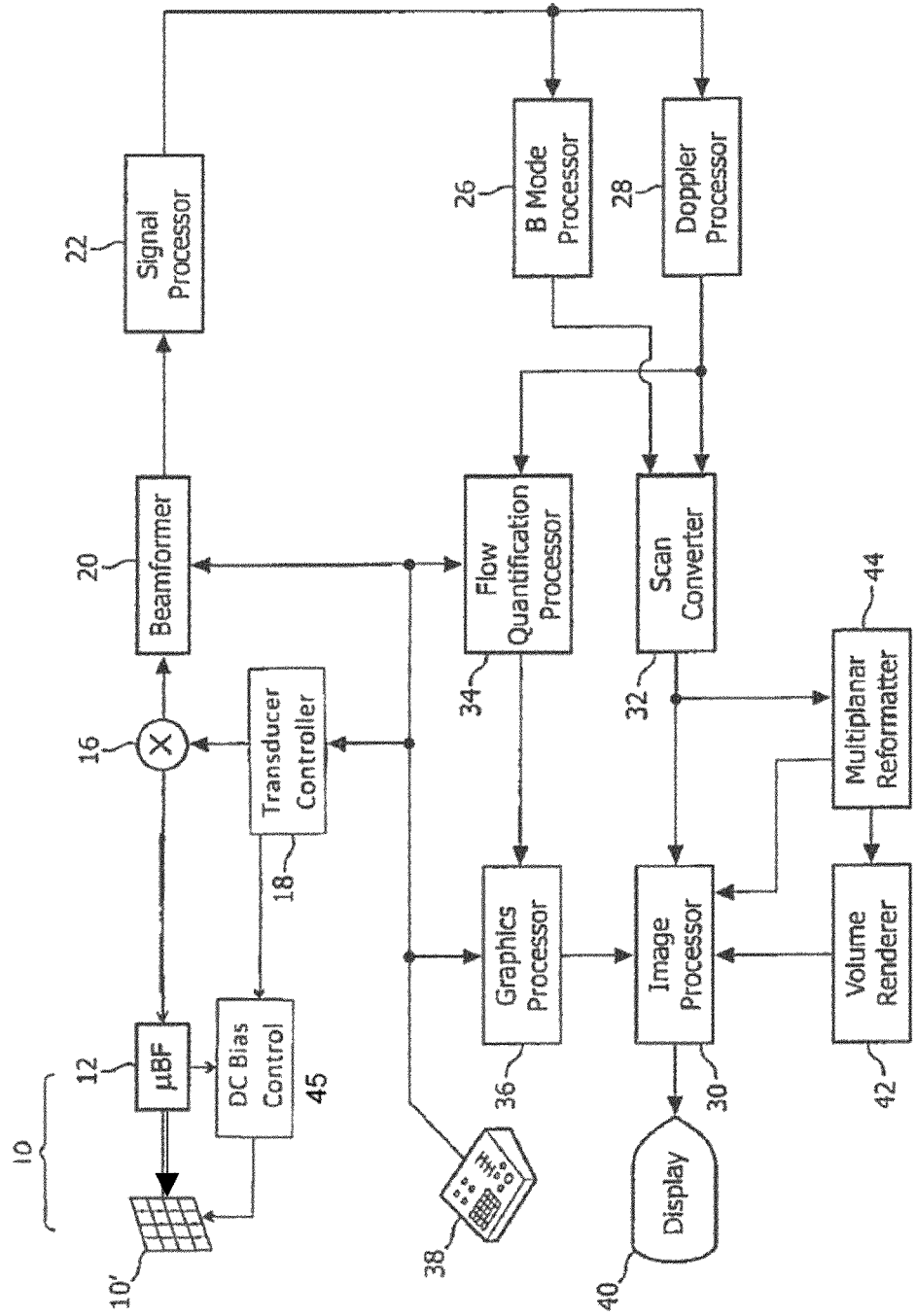
FIG. 8 illustrates in block diagram form an ultrasonic imaging system arranged to be operated in accordance with the principles of the present invention.

Referring to FIG. 8, an ultrasonic diagnostic imaging system with a CMUT array probe 10 is shown in block diagram form. The CMUT transducer array 10' is a two-dimensional array of transducer elements capable of scanning in a 2D plane or in three dimensions for 3D imaging.

In case of 3D imaging and sometimes in 2D imaging the transducer array is coupled to a microbeamformer 12 in the probe which controls transmission and reception of signals by the CMUT array cells. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled by the probe cable to a transmit/receive (T/R) switch 16 which switches between transmission and reception modes. The transmission of ultrasonic beams from the transducer array 10 under control of the microbeamformer 12 is directed by a transducer controller 18 coupled to the T/R switch and the main system beamformer 20, which receives input from the user's operation of the user interface or control panel 38. One of the functions controlled by the transducer controller is the direction in which beams are steered and focused. Beams may be steered straight ahead from (orthogonal to) the transducer array, or at different angles for a wider field of view. The transducer controller 18 can be coupled to control a DC bias control 45 for the CMUT array 10'. The DC bias control 45 controls a DC bias voltage source(s) 104 for setting DC bias voltage(s) that can be applied to the CMUT cells. The signal transmitter/receiver(s) 105 of the CMUT array can be coupled to the beamformer 20 directly or through the microbeamformer 12.

During reception the partially beamformed signals produced by the microbeamformer 12 (in case it is used) are coupled to a main beamformer 20 where partially beamformed signals from individual patches of transducer elements are combined into a fully beamformed signal. For example, the main beamformer 20 may have 128 channels, each of which receives a partially beamformed signal from a patch of dozens or hundreds of CMUT transducer cells. In this way the signals received by thousands of transducer elements of a CMUT transducer array can contribute efficiently to a single beamformed signal.

The beamformed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles. The signal processor may also perform additional signal enhancement such as speckle reduction, signal compounding, and noise elimination.

The processed signals are coupled to a B mode processor 26 and a Doppler processor 28. The B mode processor 26 employs detection of an amplitude of the received echo signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors are coupled to a scan converter 32 and a multiplanar reformatter 44. The scan converter arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field corresponding with their Doppler-estimated velocities to produce a color Doppler image which depicts the motion of tissue and blood flow in the image field. The multiplanar reformatter will convert echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.) The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow velocity values produced by the Doppler processor 28 and tissue structure information produced by the B mode processor 26 are coupled to a quantification processor 34. The flow quantification processor produces measure of different flow conditions such as the volume rate of blood flow as well as structural measurements such as the sizes of organs and gestational age. The quantification processor may receive input from the user control panel 38, such as the point in the anatomy of an image where a measurement is to be made. Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as a typed patient name. The user interface is also coupled to the transmit controller 18 to control the generation of ultrasound signals from the transducer array 10' and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

The present invention is particularly interesting for the application of CMUT cells in the ultrasound array of catheters, due to:

Miniaturization of cMUT bias related electronics;

User safety improvement. The stored charge related to the high bias voltage is isolated from the user/patient by two conductive metal plates of the third and first electrodes with a possible implementation of very high impedance series resistor.

Reduction of the system supply voltage.

This invention is also benefiting in terms of yield. As every transducer CMUT cell has its own high impedance shielding resistor inside the bias-node connection, a "failing cMUT cell" will not cause large shortcut currents and therefore will not cause breakdown of the whole array or the connected ASIC.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The invention claimed is:

1. A capacitive micromachined ultrasonic transducer cell comprising:
   a substrate
   a cell membrane opposing the substrate with a gap there between;
   a first electrode coupled to the cell membrane,
   a second electrode embedded into a cell floor opposing the first electrode and separated therefrom by a gas or vacuum cavity, wherein the cell floor comprises an upper surface of the substrate, and
   a third electrode, and
   the third electrode, which is located in the cell floor opposing the second electrode from the cavity side, wherein said third electrode is capacitively coupled with the first or second electrode, whereby the capacitive coupling is realized by a dielectric layer sandwiched between and being in direct contact with the capacitively coupled electrodes.

2. The capacitive micromachined ultrasonic transducer cell according to claim 1, wherein the capacitive relation between the second electrode and the third electrode is larger than or equals to the capacitive relation between the third electrode and the first electrode.

3. The capacitive micromachined ultrasonic transducer cell according to claim 1, wherein the dielectric layer comprises a layer of material with a high dielectric constant.

4. The capacitive micromachined ultrasonic transducer cell according to claim 1, wherein the capacitive relation between the third electrode and the first electrode is larger than the parasitic capacitance of the CMUT cell towards the substrate.

5. The capacitive micromachined ultrasonic transducer cell according to claim 1 further comprising:
   a DC source for causing a DC bias voltage to the third electrode in relation to the ground potential, and
   a signal transmitter/receiver coupled to the first electrode and the second electrodes for causing/sensing vibration of the membrane.

6. The capacitive micromachined ultrasonic transducer cell according to claim 4, wherein the DC bias source is coupled to the third electrode through a resistor.

7. The capacitive micromachined ultrasonic transducer cell according to claim 5, wherein the resistor is an on-chip resistor.

8. The capacitive micromachined ultrasonic transducer cell according to claim 6, wherein the DC bias voltage source is adapted to set the CMUT membrane to be collapsed to the cell floor during operation of the CMUT device.

9. An ultrasonic probe comprising at least one CMUT cell according to claim 1.

10. The ultrasonic probe according to claim 8, wherein the probe comprises an array of the CMUT cells, which array comprises a first and second subgroup of the CMUT cells wherein the first sub-group of CMUT cells having the first electrode interconnected along one of the two directions and the second sub-group of the CMUT cells having the second electrode interconnected along another direction.

11. The ultrasonic probe according to claim 9, wherein the third electrode of the CMUT cells in the array are coupled to a DC bias voltage source via series resistors.

12. The ultrasonic probe according to claim 10, wherein the direction of the bias electrodes interconnect to the DC bias source is the direction of the second sub-group interconnects.

13. The ultrasonic probe according to claim 11, wherein the third electrode of any of the sub-groups of the CMUT cells in the array interconnected along one of the two directions are coupled to the DC bias voltage source via one series resistor for each interconnect.

14. An ultrasonic imaging system comprising the ultrasonic probe according to claim 9.

* * * * *